(12) United States Patent
Schmued (10) Patent No.: US 6,229,024 B1
(45) Date of Patent: May 8, 2001

(54) METHOD FOR DETECTING NEURONAL DEGENERATION AND ANIONIC FLUORESCEIN HOMOLOGUE STAINS THEREFOR

(76) Inventor: Laurence C. Schmued, 200 Elizabeth Ann Dr., Pine Bluff, AR (US) 71602

( * ) Notice: Subject to any disclaimer, the term of this patent is extended or adjusted under 35 U.S.C. 154(b) by 0 days.

(21) Appl. No.: 09/234,766

(22) Filed: Jan. 21, 1999

Related U.S. Application Data (60) Provisional application No. 60/072,367, filed on Jan. 23, 1998.

(51) Int. Cl.$^7$ .................. C07D 311/80; G01N 33/566
(52) U.S. Cl. ............................ 549/391; 436/501
(58) Field of Search .............. 549/391; 436/501

(56) References Cited

U.S. PATENT DOCUMENTS

| | | | |
|---|---|---|---|
| 4,508,892 | * 4/1985 | Yoshida | 536/51 |
| 4,615,986 | * 10/1986 | Yoshida | 436/500 |
| 5,623,080 | * 4/1997 | Neckers et al. | 549/393 |
| 6,008,379 | * 12/1999 | Benson et al. | 549/224 |

OTHER PUBLICATIONS

Ali, S.F., Duhart, H.M., Newport, G.D., Lipe, G.W., and Slikker, W. Jr., Manganese–induced reactive oxygen species: Comparison between Mn$^{+2}$ and Mn$^{+3}$, Neurodegen., 4, (1995) 329–334.

Auer, R.N., Olson, Y., and Siesjo, B.K., Hypoglycemic brain injury in the rat. Correlation of density of brain damage with the EEG isoelectric time: a quantitative study, Diabetes, 33 (1984) 109–1098.

Binienda, Z., Frederick, D.L., Ferguson, S.A., Rountree, R.L., Paule, M.G., Schmued, L.C., Ali, S.F., Slikker, W. Jr., and Scallet, A.C., The effect of perinatal Hypoxia on the behavioral, neurochemical, and neurohistological toxicity of the metabolic inhibitor 3–nitropropionic acid, Metabolic Brain Disease, 10/4 (1995) 269–281.

Cammermeyer, J., The Importance of avoiding the "dark" neurons in experimental Neuropathology, Acta. Neuropath., 1 (1961) 245–270.

Chassan, J.L., Nervous System. in W.A.D. Anderson and J.M. Kissane (Eds.), Pathology, Mosby, St. Louis, 1977, pp. 2074–2148.

deOlmos, J.S., Beltramino, C.A., and de Olmos de Lorenzo, S. Use of an amino–cupric–silver technique for the detection of early and simiacute neuronal degeneration caused by neurotoxicants, hypoxia, and physical trauma, Neurotox.& Teratol., 16, (1994) 545–561.

Desai, V.G., Feuers, R.J., Hart, R.W., and Ali, S.F., MPP$^+$ induced neurotoxicity in mouse is age–dependent: Evidenced by the selective inhibition of complexes of electron transport, Brain Res., 715 (1996) 1–8.

Donaldson, J., McGregor, D., and La Bella, F., Manganese neurotoxicity: a model for free radical mediated neurodegeneration? Can. J. Physiol. Pharmacol., 60 (1982), 1398–1405.

Fink, R.P., Heimer, L., Two methods for the selective silver impregnation of degenerating axons and their synaptic endings in the centralq nervous system, Brain Res., 4, (1967) 369–374.

(List continued on next page.)

*Primary Examiner*—Deborah C. Lambkin
(74) *Attorney, Agent, or Firm*—Ralph F. Crandell (57) ABSTRACT

An anionic fluorescein homologue capable of selectively staining degenerating neurons in brain slices, the method of making the anionic fluorescein homologue, and the method of using the same for detecting neuronal degeneration. Two anionic fluorescein based fluorescent stains are the water soluble tribasic salt of a mixture of the fluorescein isomers 5-carboxyfluorescein and 6-carboxyfluorescein, and the water soluble tetrabasic salt of 5,6 dicarboxyfluorescein.

17 Claims, 8 Drawing Sheets

(8 of 8 Drawing Sheet(s) Filed in Color)

OTHER PUBLICATIONS

Fix, A.S., Horn, J.W., Wrightman, K.A., Johnson, C.A., Long, G.G., Storts, R.W., Faber, N., Wozniak, D.F., and Olney, J.W., Neuronal vacuolization and necrosis induced by the non–competitive N–methyl–D–aspartate (NMDA) antagonist MK (+) 801 (dizocilpine maleate): a light and electron microscopic evaluation of the rat retrosplenial cortex, Exp. Neurol., 123 (1993) 204–215.

Gallyas, F., Wolf J.R., Bottcher, H., and Zaborsky, L., A reliable and sensitive method to localize terminal degeneration and lysosomes in the central nervous system, Stain Technol., 55 (1980) 299–306.

Garcia, J.H. and Kamijiyo, Y., Cerebral infraction: Evolution of histopathological changes after occlusion of a middle cerebral artery in primates, J. Neuropathol. Exp. Neurol., 33 (1974) pp. 409–421.

Gary, L.J. and Powell, T.P.S., The projections of the retina in the cat, J. Anat. (Lond.) 102 (1968) 189–222.

Hamilton, B.F. and Gould, D.H., Nature and distribution of brain lesions in rats intoxicated with 3–nitropropionic: a type of hypoxic (energy deficient) brain damage, Acta Neuropathol., 72 (1987) 286–297.

Heikkila, R.E., Hess A., and Duvoisin R.C., Dopaminergic neurotoxicity of 1–methyl–4–phenyl–1,2,5,6–tetrahydropyridine in mice, Science, 224 (1983) 1451–1453.

Kindt, M.V., Nickels, W.J., Sonsalla, P.K., and Heikkila, R.E., Mitochondria and the neurotoxicity of MPTP, Trends Pharmacol. Sci., 7 (1986) 473–475.

Lillie, R.D., and Fullmer, H.M., Histopathologic technique and practice, McGraw–Hill, New York, 1976, pp. 208–209.

Nauta, W.J.H. and Gygax, P.A., Silver impregnation of degenerating axons in the central nervous system: A modified technique, Stain Technol., 29 (1954) 91–93.

O'Hearn, E. and Molliver, M.E., Degeneration of Purkinje cells in parasagital zones of the cerebellar vermis after treatment with ibogaine or harmaline, Neurosci., 55 (1993) 303–310.

Olney, J.W., Labruyere, J., and Price, M.T., Pathological changes induced in cerebrocortical neurons by phencyclidine and related drugs, Science, 244 (1989) 1360–1362.

Olney, J.W., Labruyere, J., Wang, G., Sesma, M.A., Wozniak, D.F., and Price, M.T., NMDA antagonist neurotoxicity: mechanism and protection, Science, 254 (1991) 1515–1518.

Olney, J.W., Rhee, V., Ho, O.L., Kainic acid, : A powerful neurotoxic analogue of glutamate, Brain Res., 77, 1974, 507–515.

Scallet, A.C., Ye, X., Rountree, R., Nony, P. and Ali, S.F., Ibogaine produces neurodegeneration in rat, but not mouse, cerebellum: Neurohistological biomarkers of Purkinje cell loss, Ann NY Accad. of Sci., in press.

Schmued, L.C., Sawchenko, P.E., and Swanson, L.W., Some fluorescent counterstains for neuroanatomical studies, J. Histochem. Cytochem. 3012 (1982) 123–128.

Schmued, L.C., and Fallon, J.H., "Fluoro–Gold", a new fluorescent retrograde axonal tracer with numerous unique properties, Brain Res., 377 (1986) 147–154.

Schmued, L.C., Scallet, A.C., and Slikker, W. Jr., Domoic acid–induced neuronal degeneration in the primate forebrain revealed by degeneration specific histochemistry, Brain Res., 695 (1995) 64–70.

Schmued, L., Scallet, A., Ali,S., and Slikker W. Jr., Localization of domoic acid induced neuronal degeneration in the primate forebrain as revealed by conventional silver methodologies and by a novel fluorescent technique, Soc. for Neurosci. Abs., 19/2 (1993) 1322.

Siesjo, B.K., Cell damage in the brain: a speculative synthesis, Cereb. Blood Metabol., 1 (1981) 155–185.

Sloot, W.N., van der Sluijs–Gelling, A.J., and Gramsbergen, Selective lesions by manganese and extensive damage by iron after injection into rat straitum or hippocampus, J. of Neurochem., 62 (1994) 205–216.

Stensaas, S.S., Edwards, C.Q., and Stensaas, L.J., An experimental study of hyperchromic nerve cells in the cerebral cortex, Exp. Neurol., 36 (1972) 472–487.

Tryphonas, L., Truelove, J., Todd, E., and Iverson, F., Acute neurotoxicity of domoic acid in the rat, Toxicol. Pathol., 18 (1990) 1–9.

Dreschsler,G. and Smagin, S., Preparation of trimelliteins and 5–carboxy fluorescein, J. Praktische Chem., 28 (1965) 513, 21.

Schmued, L.C., Scallet, A., Ali, S., Binienda, Z., Bowyer, J., and Slikker Jr., W., Development and characterization of two histochemical techniques for the respective detection fo neuronal and myelin degeneration, Society for Neuroscience, Abstracts 1995.

Schmued, L.C., Scallet, A., Slikker Jr., W., and Binienda, Z., Distribution of 3–Nitropropionic acid (3–NPA) induced degeneration of myelinated axons and terminals: A combined Fluoro–Jade and AuCl3 study, Society for Neuroscience, Abstracts 1996.

Schmued, L.C., Albertson, C., Slikker Jr., W., Fluoro–Jade: a novel fluorochrome for the sensitive and reliable histochemical localization of neuronal degeneration, Brain Research 751 (1997) 37–46, Pub. Mar. 14, 1997.

CA109:170254, Abbott Labs, USA, 1988.*

* cited by examiner

METHOD FOR DETECTING NEURONAL DEGENERATION AND ANIONIC FLUORESCEIN HOMOLOGUE STAINS THEREFOR

CROSS REFERENCE TO RELATED APPLICATIONS

This application claims the benefit of Provisional Application Ser. No. 60/072,367, filed Jan. 23, 1998, by Laurence C. Schmued, for Method of Detecting Neuronal Degeneration and Fluorescein Type Stain Therefor.

BACKGROUND OF THE INVENTION

1. Field of the Invention

The present invention relates to a method for the postmortem detection and localization of degenerating neurons in brain slices, and more particularly to anionic fluorescent type homologue therefor.

2. Prior Art

Many neuroscientists including toxicologists, pathologists, pharmacologists, anatomists and histochemists share an interest in detecting neuronal degeneration. The demonstration of this phenomenon, however, is often difficult from both a technical and an interpretational point of view. Conventional techniques such as H&E (hematoxylin and eosin), or Nissl type stains (crystal violet, thionin, etc.) are technically simple and can be used to infer degeneration based on changes such as neuronal shrinkage, vacuolation, and hyperchromatism. Chassan, J. L., "Nervous System" in W. A. D. Anderson and J. M. Kissane (Eds.), *Pathology*, Mosby, St. Louis, 1977, pp. 2074–2148; Garcia, J. H. and Kamijiyo, Y., "Cerebral Infraction: Evolution of Histopathological Changes After Occlusion of a Middle Cerebral Artery in Primates," J. Neuropathol. Exp. Neurol., 33 (1974) pp. 409–421; and Siesjo, B. K., "Cell Damage in the Brain: a Speculative Synthesis," Cereb. Blood Metabol., 1 (1981) 155–185. Unfortunately, such changes are not necessarily indicative of neuronal degeneration and may be due to processing artifacts or non-lethal alterations in cellular morphology. Processing artifacts can result in both shrunken and hyperchromatic cells. Cammermeyer. J., "The Importance of Avoiding the "dark" Neurons in Experimental Neuropathology," Acta. Neuropath. 1 (1961) 245–270; and Stensaas, S. S., Edwards, C. Q., and Stensaas, L. J., "An Experimental Study of Hyperchromic Nerve Cells in the Cerebral Cortex," Exp. Neurol., 36 (1972) 472–487. Not only are such techniques prone to false positives, but it is also possible to miss degenerating neurons since all cells stain with these dyes while only relatively subtle morphological differences exist between normal and degenerating neurons. These interpretational difficulties make the analysis of conventionally stained material time consuming. In contrast, suppressed silver techniques are much better from this point of view in that normal neurons remain unstained while degenerating neurons stain black. de Olmos, J. S., Beltramino, C. A., and de Olmos de Lorenzo, S. "Use of an amino-cupric-silver technique for the detection of early and simiacute neuronal degeneration caused by neurotoxicants, hypoxia, and physical trauma," Neurotox.& Teratol., 16, (1994) 545–561; Fink, R. P., Heimer, L., "Two methods for the selective silver impregnation of degenerating axons and their synaptic endings in the central nervous system," Brain Res., 4, (1967) 369–374; Gallyas, F., Wolf J. R., Bottcher, H., and Zaborsky, L., "A reliable and sensitive method to localize terminal degeneration and lysosomes in the central nervous system," Stain Technol., 55 (1980) 299–306; and Nauta, W. J. H. and Gygax, P. A., "Silver impregnation of degenerating axons in the central nervous system: A modified technique," Stain Technol., 29 (1954) 91–93. The main drawbacks associated with suppressed silver techniques lie in their labor intensive and capricious nature.

OBJECTS OF THE INVENTION

The principal object of the present invention is to provide an improved histochemical tracer which is simple and reliable to use as well as highly sensitive and easy to interpret.

Another object of the present invention is to provide an improved histochemical tracer of the foregoing character which is a sensitive and definitive marker of neuronal degeneration.

A further object of the present invention is to provide an improved histochemical tracer of the foregoing character which is simple to use and produces reliable results.

SUMMARY OF THE INVENTION

The present invention is embodied in an anionic fluorochrome capable of selectively staining degenerating neurons in brain slices, the method of making the anionic fluorochrome, and the method of using the same for detecting neuronal degeneration. The histochemical application of this fluorochrome results in a simple, sensitive and reliable method for staining degenerating neurons and their processes. The technique will detect neuronal degeneration resulting from exposure to a variety of neurotoxic insults. The fluorochrome can be combined with other fluorescent methodologies including immunofluorescence, fluorescent axonal tract tracing, and fluorescent Nissl counterstaining. Compared to conventional methodologies, the fluorochrome of the present invention is a more sensitive and definitive marker of neuronal degeneration than conventional H&E or Nissl type stains, while being comparably sensitive yet considerably simpler and more reliable than suppressed silver techniques.

The novel anionic fluorochorme of the present invention is more specifically a tri- or tetra-salt, such as a sodium salt of a 5/6-carboxy fluorescein. The fluorochrome may for example be trisodium 5/6-carboxy fluorescein or tetrasodium 5/6-carboxy fluorescein.

DESCRIPTION OF THE DRAWINGS

The file of this Patent contains at least one drawing executed in color. Copies of this patent with color drawings will be provided by the Office upon request and payment of the necessary fee.

DESCRIPTION OF THE INVENTION

The two anionic fluorescein based fluorescent stains embodying the present invention are 1) the water soluble, tribasic salt of a mixture of the fluorescein isomers 5-carboxyfluorescein and 6-carboxyfluorescein and 2) the water soluble tetrabasic salt of 5,6 dicarboxyfluorescein. The two preferred fluorescent stains of the present invention are the trisodium fluorescein salt, trisodium 5/6-carboxyfluorescein, which has the following structure:

And the tetrasodium 5,6-tricarboxyfluorescein which has the following structure:

The abovetrisodium 5,6-carboxyfluorescein and tetrasodium 5,6-carboxyfluorescein both provide a simple, sensitive, and reliable new method for demonstrating and localizing neuronal degeneration.

The respective tribasic and tetrabasic salts of 5/6-carboxyfluorescein and 5,6-dicarboxyfluorescein embodying the present invention may be shown by the following general formula:

wherein $R_1$ and $R_2$=—COOX, or —H (provided that both do not=—H), or and X=$Na^+$, $K^+$, $Li^+$, or $NH_4^+$.

The foregoing formulae represent compounds found to be effective anionic fluorescein based fluorochromes for staining and detecting degenerating neurons. The nomenclature for the R groups in the 5 and 6 carbon positions is also sometimes referred to as the 4 and 5 carbon positions by some chemists.

An isomer alone will work equally well for detecting neuronal degeneration. The mixture, however, is less expensive to manufacture. The sodium salt of carboxy fluorescein is preferred, although other common cations like potassium, lithium, or ammonium will also work. The following is a list of related compounds which will function similarly, from the most general (preferred) to the most specific:

(a.) All salts (e.g. Na, K, Li, $NH_3$) of all fluorescein molecules with anionic substitutions (eg. carboxyl).
(b.) All salts of fluorescein with anionic substitution in the 5 and/or 6 position.
(c.) All salts of fluorescein with carboxy group substitutions.
(d.) All salts of fluorescein with carboxy group substitutions in the 5 and/or 6 positions.
(e.) The sodium salts of fluorescein with carboxy group substitution in the 5 and/or 6 position.
(f.) The trisodium and tetrasodium salts of fluoroscein with a carboxy group substitution in the 5 and/or 6 position.

To prepare the preferred trisodium salt of 5/6 carboxyfluorescein, one gram of 5/6-carboxyfluorescein is suspended in 10 ml of distilled water. While stirring, 3.4–3.6 ml of 9% NaOH is slowly added to achieve a final pH between 7.0 and 8.0, indicating a 1:3 molar ratio of carboxyfluorescein ions to sodium ions, and with the dye fully dissolved. The dye is then reconstituted via vacuum lyophilization or evaporation at 45° C. The deep red crystals, with a metallic green iridescence, thus produced are collected and homogenized with a mortar and pestle and stored, in sealed containers in a desiccator.

Alternatively, either chromatographically purified 5-carboxyfluorescein or 6-carboxyfluorescein can be used as a starting material instead of the mixed isomers. The individual isomers are processed the same as previously described for the mixture of 5/6-carboxyfluorescein.

A more labor intensive, but less expensive alternative way to make the carboxy fluorescein of the present invention is to synthesize the starting material, 5/6-carboxyfluorescein. Two moles of resorcinol and one mole of 1,2,4-benzenetricarboxylic anhydride are ground together. The mixture is then heated to 180° C., causing it to melt and subsequently fulminate. After two hours at this temperature, the fused reaction product is allowed to cool and is then pulverized. The result is 5/6-carboxyfluorescein, which can then be converted to the salt as described above. Alternative salts can be made by titrating with the hydroxides or carbonates of other cations such as potassium, lithium, and ammonium. The exact concentration of the solutions is not critical, as long as the correct stoichiometry is maintained. Also, the water can be removed by means other than evaporation such as by lyophilization.

Two modified compounds embodying the present invention, which are also carboxyfluorescein derivatives and may be even more sensitive markers of neuronal degeneration, are the dicarboxy and the bis xanthenone analogues. Specifically the carboxy homologue corresponds to the tetrasodium 5,6-carboxyfluorescein molecule illustrated above. The bis xanthenone homologue corresponds to the molecule having the general formula illustrated above where one R group is COOX and the other R group is 3'-hydroxy-6'-ketoxanthenone. The sodium salt of this compound has the formula:

More generally, the fluorescein compound has the structure:

wherein one R group consists of COOX and the other R group is selected from the group consisting of COOX, 3'hydroxy-6'ketoxanthenone, and hydrogen, and X is selected from the group consisting of $Na^+$, $K^+$, $Li^+$, and $NH_3^+$.

These related anionic fluorescein homologues are simultaneously synthesized by pulverizing and mixing together two or more moles of resorcinol with one mole of 1,2,4,5-benzenetetracarboxylic dianhydride. The mixture is heated to 180° C. for two hours. The fused mass is cooled, pulverized, and mixed with distilled water to form a 10% suspension. To this suspension a 9% solution of sodium hydroxide is added in drop wise fashion until a neutral pH is achieved. After two hours at room temperature, the solution is filtered to remove any insoluble material, and then dehydrated with heat (60° C.) or vacuum lyophilization. The resulting dark red crystals are pulverized and stored in a desiccator at room temperature.

The utility of the above described anionic fluorescein stains embodying the present invention is clear from the following tests utilizing either the preferred trisodium 5/6-carboxyfluorescein or the preferred tetrasodium 5,6-dicarboxyfluorescein. In this description, both the trisodium 5/6-carboxyfluorescein and the tetra sodium 5,6-dicaroxyfluorescein prepared as described above are sometimes collectively referred to for convenience as TSCF.

Materials and Methods

Animals: All experiments used adult (3–6 months old) male Sprague-Dawley rats except for studies on MPTP which used adult C-57 mice. Animals were given ad libritrum food and water. All animals were used in accordance with the Institutional Animal Care and Use Guidelines.

Drugs: This study employed the following neurotoxicants which were obtained from Sigma Chemical Company, Saint Louis Mo., unless otherwise indicated: 1) Kainic acid (9 mg/kg) was administered i.p. and rats were sacrificed 1 to 7 days later. 2) Domoic acid (1–3 mg/kg), prepared by Dr. Sherwood Hall of the Food and Drug Administration, was administered i.p. and animals were sacrificed 4 hours or 7 days post drug administration. 3) Ibogaine (100 mg/kg) was given i.p. and the animals were sacrificed 1 day or 1 week post drug administration. 4) PCP (phencyclidine) (50 mg/kg) and MK-801 (5 mg/kg), from Research Biochemicals International, Natick Mass., were both given i.p. and the animals were sacrificed 1 day or 1 week after drug exposure. 5) 3-NPA (3-nitropropionic acid) was given as a single subcutaneous dose of 30 mg/kg and the animals were perfused one to five days later. 6) MPTP (1-methyl-4-phenyl-1,2,3,6-tetrahydropyridine) from Research Biochemicals International, Natick Mass., was administered as a single 50 mg/kg i.p. dose and the animals were perfused 1, 2, or 5 days later.

Stereotaxic Injection: Six animals were injected with 0.05 ul of 0.05 M manganese acetate or manganese chloride into the striatum, while a similar volume and concentration of iron chloride or iron sulfate was injected into the contralateral striatum. These multivalent metal salts were injected stereotaxically with a Hamilton microsyringe over a ten minute time interval while animals were under deep Ketamine (75 mg/kg) and Rompun (9 mg/kg) anesthesia. The animals were perfused two days later.

Enucleation: Two animals were anesthetized with the aforementioned anesthetic and the left eye was enucleated. One week later the animals were perfused with buffered formalin and their brains were removed and postfixed in fixative solution plus 20% sucrose.

Controls: Six animals received a single i.p. injection of physiological saline and were perfused 2 days later.

Histological Processing: Animals were anesthetized with Ketamine and Rompun, as described above, and the majority were perfused with 500 ml of 0.1 M neutral phosphate buffered formaldehyde (4%). A few of the kainic acid dosed animals were perfused with 4% formaldehyde in carbonate buffer (pH 11, 0.1 M), and a few animals were anesthetized and their brains removed without fixation. Brains to be cut on a freezing sliding microtome were postfixed in the fixative solution plus 20% sucrose and cut into 20–40 um thick sections which were collected in buffer solution. Cryostat sections were cut at 15 um thickness and mounted directly on gelatin coated slides. Unfrozen vibratome cut sections were cut at 50 um thickness and collected in buffer solution. Tissue for paraffin embedding was dehydrated with gradated alcohols, cleared with xylene, and infiltrated with paraffin overnight. This paraffin embedded tissue was then cut into 8 um thick sections which were mounted on slides, deparaffinized with xylene and rehydrated in gradated alcohols prior to staining.

Fluorescein Dye: Trisodium 5/6-carboxyfluorescein dye embodying the present invention, a TSCF dye, can be obtained from Histo-Chem, Inc. P.O. Box 183, Jefferson, Ark. 72079 under the trademark FLUORO-JADE. This product is an anionic tribasic fluorescein derivative with a molecular weight of 445 Daltons. It has an emission peak at 550 nm and excitation peaks at 362 and 390 nm respectively. The dry powder is stable when stored in the dark in an air tight container. The 0.01% stock solution is stable for at least 2 months when stored in the refrigerator, in contrast to the working solution which should be used the same day as prepared.

Staining Procedure: Brain sections were mounted with distilled water onto gelatin coated slides and dried on a slide warmer at 45° C. The tissue was fully dry within 20 minutes at which time it was immersed in 100% ethyl alcohol for 3 minutes followed by a one-minute change in 70% alcohol and a one-minute change in distilled water. The slides were then transferred to a solution of 0.06% potassium permanganate for 15 minutes and were gently shaken on a rotating platform. This solution when kept in a sealed glass container remains usable for a period of about one week. The slides were rinsed for one minute in distilled water and were then transferred to the TSCF staining solution where they were gently agitated for 30 minutes. A 0.01% stock solution of the dye was prepared by dissolving 10 mg TSCF in 100 ml of distilled water. The 0.001% working solution of TSCF was prepared by adding 10 ml of the stock TSCF solution to 90 ml of 0.1% acetic acid in distilled water. After staining, the sections were rinsed with 3 one-minute changes of distilled water. Excess water was drained off, and the slides were rapidly air dried on a slide warmer or with a hot air gun. When dry, the slides were immersed in xylene and then coverslipped with D.P.X. (Aldrich Chem. Co. of Milwaukee Wis.) mounting media. Sections were examined with an epifluorescence microscope using a filter system suitable for visualizing fluorescein or FITC. The resulting slides were quite stable and required no special storage conditions or anti-quench agents. The potassium permanganate pretreatment further enhanced the permanence of the preparation resulting in extremely slow fading, even under high magnification epifluorescent illumination.

Staining Variations for Multiple Label Studies: Although the aforementioned staining protocol has been deemed to be of optimal sensitivity, resolution, and contrast, it may be that some aspects of the pretreatment procedure are incompatible with other desired histological endpoints. It should therefore be emphasized that the procedure is basically quite flexible. The pretreatment procedure with ethanol and potassium permanganate serve to reduce background staining, but may also inhibit costaining with immunofluorescent, fluorescent Nissl, and fluorescent axonally transported tracers. The pretreatment steps may be omitted if alternative measures are taken to reduce background staining. Alternative ways to reduce background staining include the use of high pH formalin fixation (e.g. 0.1 M, pH 11 sodium carbonate vehicle), low dye concentration (e.g. 0.0001%), low temperature (e.g. 5° C.) of staining solution, and long post staining rinses with distilled water (e.g. 3 changes of 3 minutes each). Multiple labeling with fluorescent retrograde axonally transported tracers such as the tracer described and claimed in U.S. Pat. No. 4,716,905, and sold under the trademark "Fluoro-Gold" by Fluorochrome Inc, Denver, Colo., was achieved by combining the standard procedure used to demonstrate retrograde axonal transport of the "Fluoro-Gold" tracer with the aforementioned TSCF procedure. Briefly, animals were anesthetized with Ketamine (75 mg/kg) and Rompun (20 mg/ml) and then received 0.1 ul of 2.5% "Fluoro-Gold" tracer injected stereotaxically into the hippocampus or the lateral septum. Two days later the animals were given kainic acid and were subsequently perfused with neutral buffered formalin fixative the following day. Sections containing retrogradely transported "Fluoro-Gold" tracer were then stained with TSCF without ethanol and potassium permanganate pretreatment. Fluorescent Nissl counterstaining of non-degenerating cells was accomplished with the use of ethidium bromide or DAPI. Schmued, L. C., Sawchenko, P. E., and Swanson, L. W., "Some Fluorescent Counterstains for Neuroanatomical Studies," J. Histochem. Cytochem. 3012 (1982) 123–128.

Briefly, a 0.01% stock solution of ethidium bromide or DAPI (4',6-diamidino-2-phinylindole) obtained from Aldrich Chemical Company, Milwaukee, Wis., was prepared in distilled water, and the appropriate amount was added directly to the TSCF staining solution. The final DAPI concentration should be 0.0002% whereas the final ethidium bromide concentration should be 0.00005%. Nuclear counterstaining with DAPI can be accomplished following pretreatment with potassium permanganate while ethidium bromide Nissl counterstaining requires omission of the pretreatment step. Another multiple labeling technique involved combining standard immunofluorescent methods with TSCF histochemistry. For this study, loose or slide mounted tissue was first rinsed with two five minute changes of vehicle (phosphate buffered saline with 2% normal swine serum) and then incubated in a primary antibody for 1–3 days at 50° C. For this study, an antibody to GFAP (Dako A/S, Denmark) was used at a dilution of 1:200 in vehicle. The sections were then rinsed with two five minute changes of vehicle, and subsequently immersed for 45 minutes in a room temperature secondary antibody solution consisting of a rhodamine conjugated swine anti-rabbit antibody (Dako A/S, Denmark) diluted 1:30 in a vehicle. The tissue was then rinsed with 2 five-minute changes of 0.9% saline before being processed for TSCF histochemistry. Pretreatment with ethanol and potassium permangenate tended to reduce the immunoreactivity of the GFAP immunocytochemistry and therefore was generally omitted. The background staining was minimized by using a staining solution of low dye concentration (0.0001%) and a low temperature (50° C.).

Conventional Brightfield Techniques: For purposes of comparison, two conventional Brightfield histological procedures were applied to the hippocampus of the same kainic acid dosed animals that were examined with the TSCF staining procedure. H&E staining of paraffin processed 4 to 8 um thick tissue sections employed the standard unacidified variant. Lillie, R. D., and Fullmer, H. M., Histopathologic Technique and Practice, McGraw-Hill, New York, 1976, pp. 208–209.

Suppressed silver staining of neuronal degeneration was achieved by application of the de Olmos' cupric silver technique to 35 um thick frozen sections. de Olmos, J. S., Beltramino, C. A., and de Olmos de Lorenzo, S. "Use of an amino-cupric-silver technique for the detection of early and simiacute neuronal degeneration caused by neurotoxicants, hypoxia, and physical trauma," Neurotox.& Teratol., 16, (1994) 545–561.

Results

Conventional Histological Methods

Figure 1:
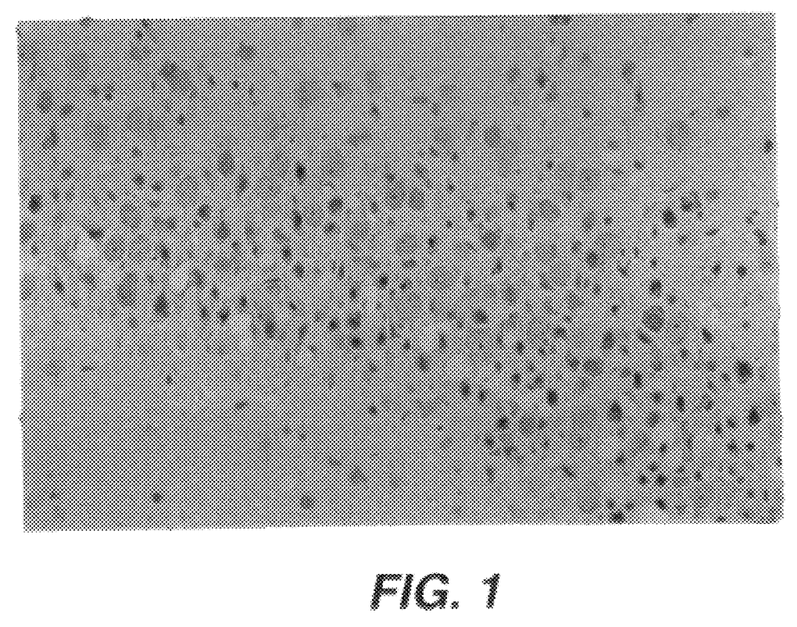
FIG. 1 is a color photomicrograph of a Hematoxylin and Eosin stained paraffin embedded section of the hippocampus of a rat 24 hours after exposure to kainic acid; Brightfield; Mag. bar=200 um.

1) H&E Staining of paraffin processed tissue resulted in the staining of all brain components. Nuclei are typically stained blue with hematoxylin, while the cell cytoplasm and neuropil stain red with eosin. Kainic acid exposure resulted in the altered morphology of some hippocampal pyramidal neurons of the CA1 region (FIG. 1). Some neurons exhibit large round nuclei with conspicuous nucleoli and a difficult to define cytoplasm. Other neurons exhibit a more shrunken and hyperchromatic nucleus which may or may not be accompanied by a hypereosinophilic cytoplasm.

Figure 2:
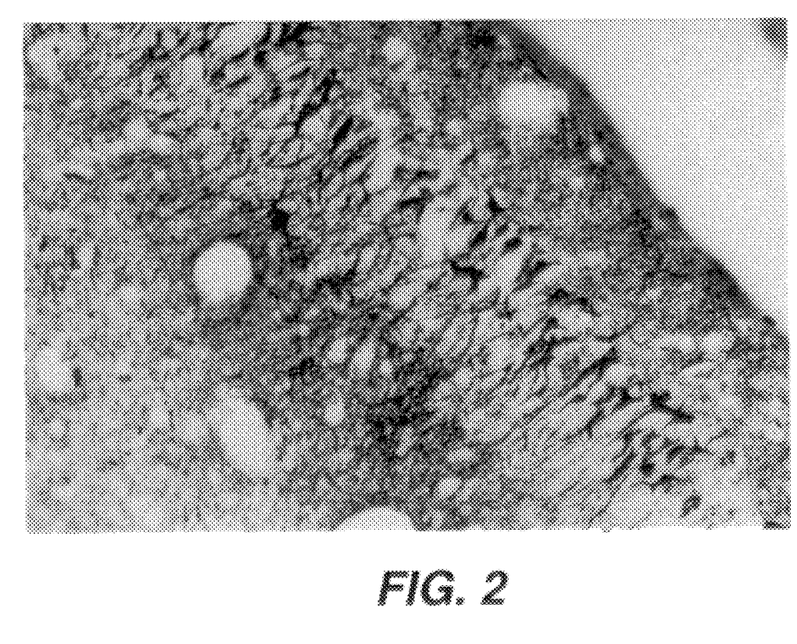
FIG. 2 is a color photomicrograph of de Olmos suppressed cupric-silver technique labeled, degenerating pyramidal cells, in frozen section taken from the hippocampus contralateral to that shown in FIG. 1, degenerating neurons appearing black, while normal neurons are unstained; Brightfield; Mag. bar=200 um.
Figure 3:
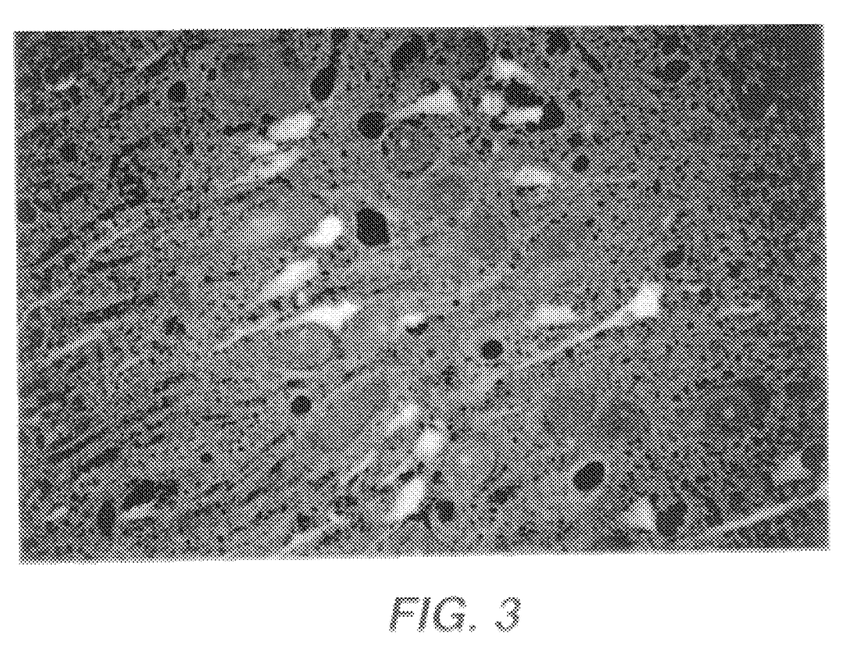
FIG. 3 is a color photomicrograph of paraffin embedded kainic acid treated tissue as shown in FIG. 1, stained with the anionic fluorescein homologues embodying the present invention, degenerating hippocampal pyramidal cells appearing in bright yellow-green, while normal neurons appear even darker than background with a lightly staining nucleoli; FITC filter; Mag. bar=100 um.
Figure 4:
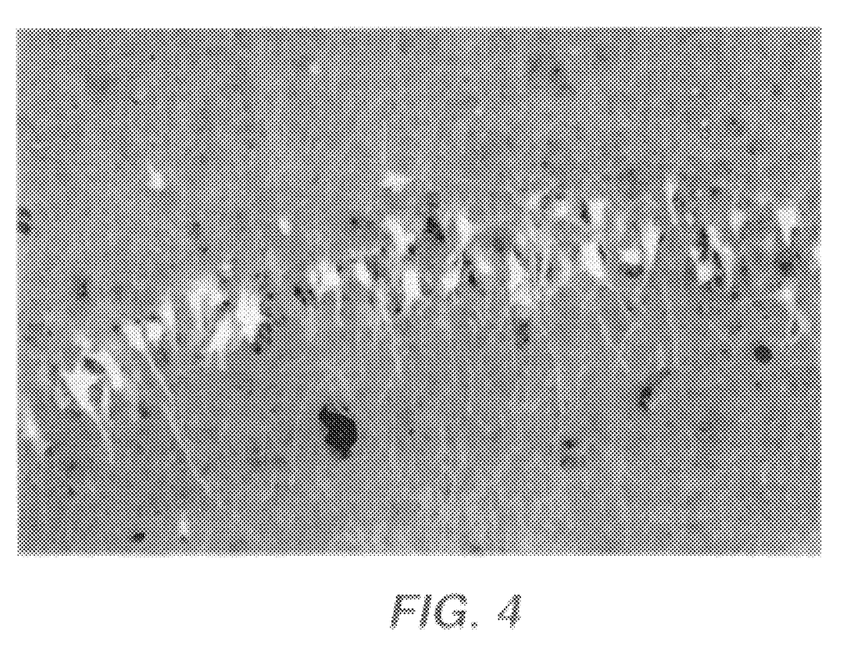
FIG. 4 is a color photomicrograph of degenerating hippocampal neurons from the same kainic acid treated frozen sections shown in FIG. 2, stained with an anionic fluorescein homologue stain embodying the present invention; degenerating neurons and their dendrites exhibiting a bright yellow-green fluorescence while healthy neurons are unstained; FITC filter; Mag. bar=200 um.

2) The de Olmos' cupric-silver method resulted in the selective staining of a subset of hippocampal neurons (FIG. 2) in animals dosed systemicly with kainic acid. These neurons, their proximal dendrites and terminal-like puncta appear opaque against a light background. Non-specific staining often resulted in some artifactual staining of mitochondria, nucleoli, and myelin. This was seen most frequently in tissue that had been postfixed for less than one month.

Figure 5:
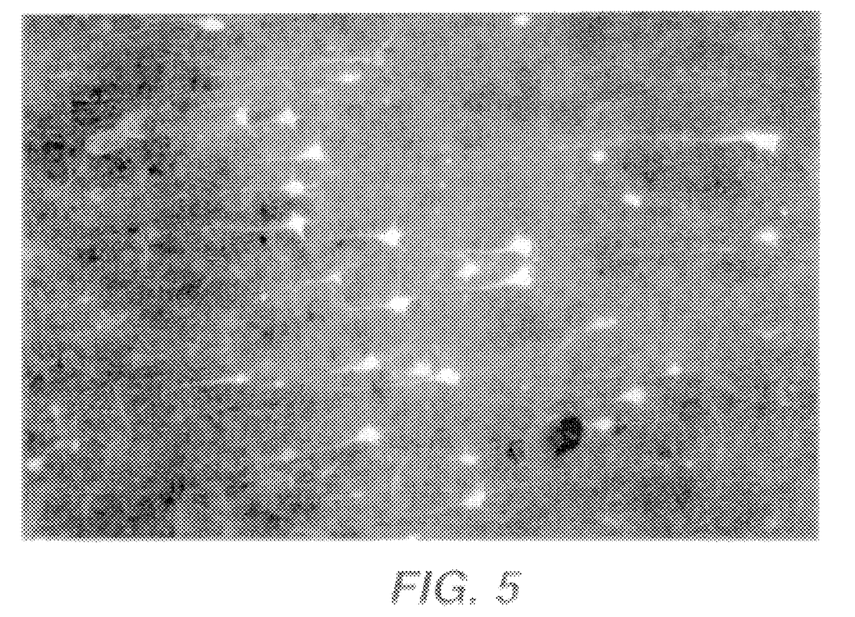
FIG. 5 is a color photomicrograph of kainic acid exposed tissue stained with an anionic fluorescein homologue stain embodying the present invention and showing positive pyramidal cells in parietal cortex; FITC filter; Mag. Bar=200 um.
Figure 6:
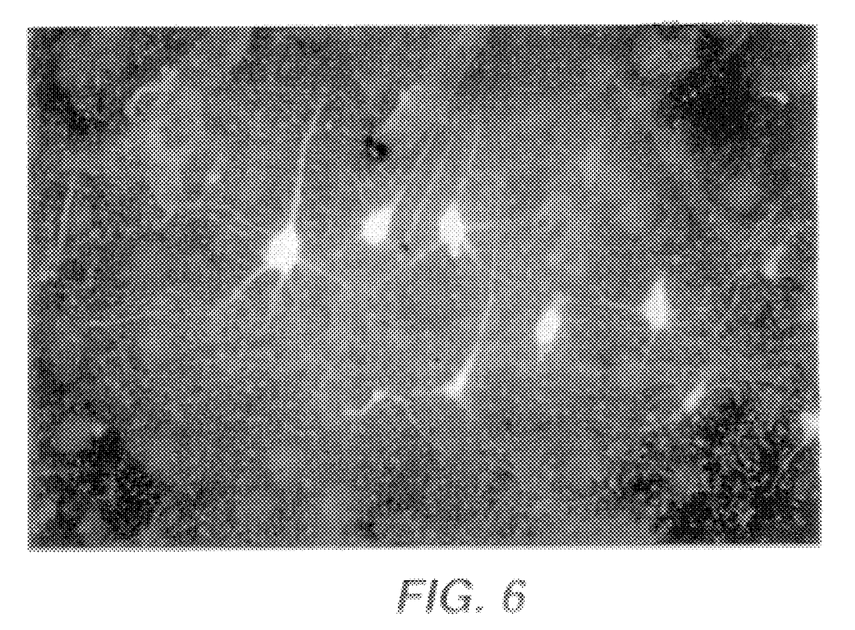
FIG. 6 is a color photomicrograph of higher magnification of the cortical degeneration revealing proximal dendrites and terminal-like puncta; FITC filter; orientation: 90 degree rotation; Mag. bar=100 um.
Figure 7:
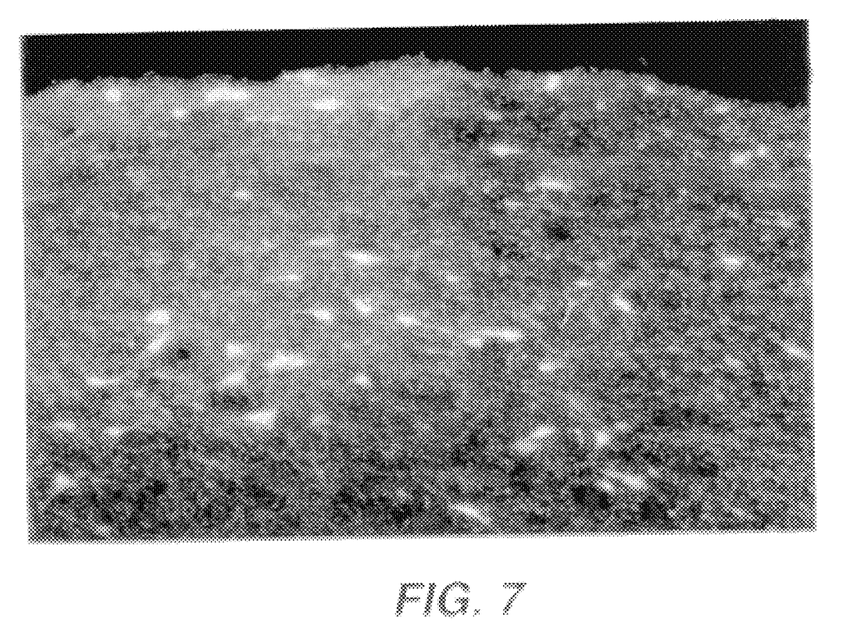
FIG. 7 is a color photomicrograph of the dorsal lateral thalamus of a rat treated with kainic acid four days prior to sacrifice, wherein staining with the anionic fluorescein homologue stain of the present invention reveals numerous positive cells and terminals; FITC filter; Mag. bar=200 um.
Figure 8:
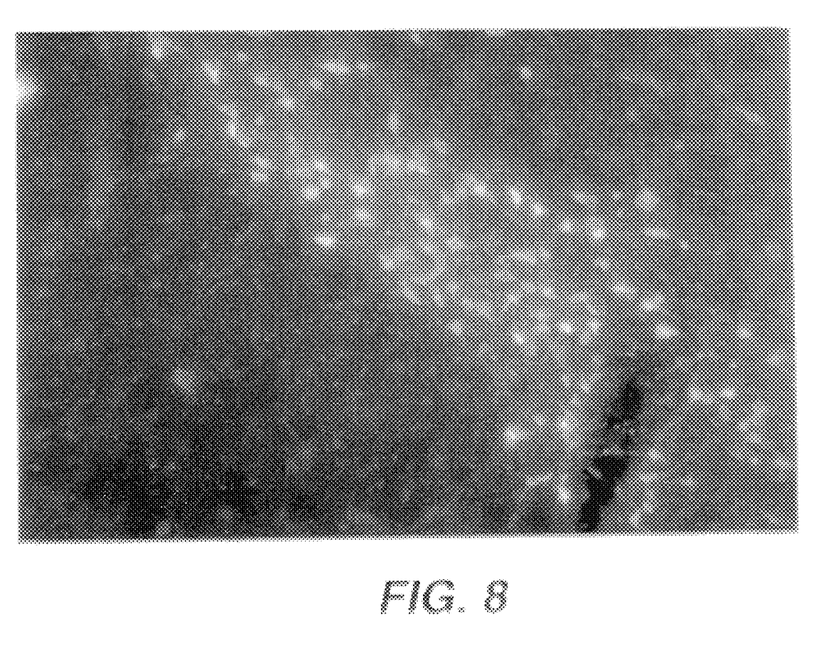
FIG. 8 is a color photomicrograph of the substantia nigra of a mouse treated with MPTP wherein staining with an anionic fluorescein homologue stain of the present invention reveals numerous positive neurons within the pars compacta and ventral tegmental region; FITC filter; Mag. bar=200 um.
Figure 9:
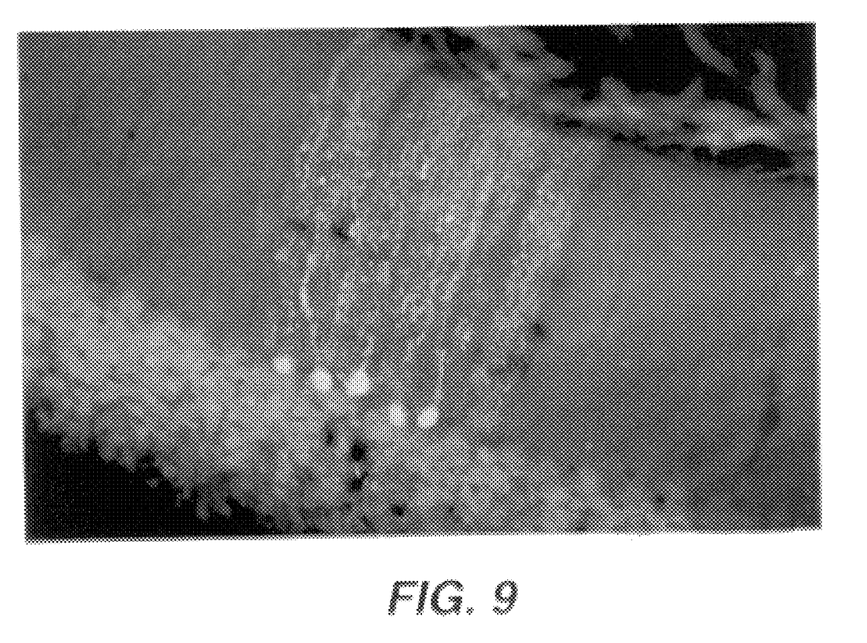
FIG. 9 is a color photomicrograph showing selected patches of Purkinje cells and their dendrites in the medial cerebellum indicating ibogaine induced degeneration revealed by staining with an anionic fluorescein homologue stain embodying the present invention; Sagittal orientation; FITC filter; Mag. bar=200 um.
Figure 12:
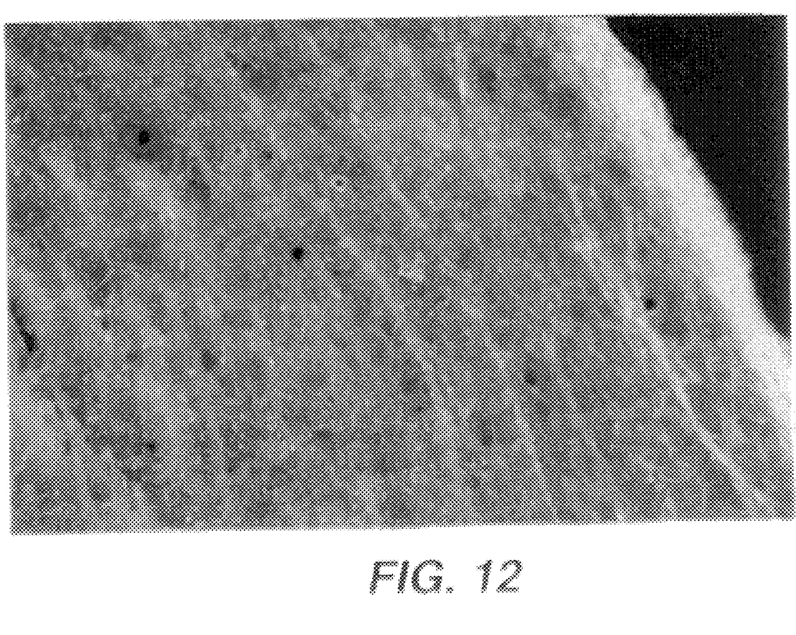
FIG. 12 is a color photomicrograph of the same brain as shown in FIG. 11 and revealing an attenuated optic tract at the most lateral aspect of the caudal diencephalon, staining with an anionic fluorescein homologue stain of the present invention showing medially positive axons and terminal-like puncta throughout the lateral geniculate nucleus contralateral to the enucleated eye; FITC filter; Mag. bar=200 um.

Trisodium 5/6-carboxyfluorescein and Tetrasodium 5,6-dicarboxyfluorescein Staining In general the staining pattern seen with TSCF corresponds to the pattern of argyrophilia seen with an ideal suppressed silver method. TSCF stains the cell bodies, dendrites, axons and axon terminals of degenerating neurons but does not stain healthy neurons, myelin, vascular elements or neuropil. Cells of the meninges and the choroid plexus exhibit an affinity for TSCF. Unlike the silver methods in which degenerating neurons appear dark against a light background, degenerating neurons stained with TSCF appear bright green against a dark background (FIGS. 3–8). Thicker sections (40–100 um) allow for the visualization of dendritic arborizations (FIGS. 4 and 9), while thinner sections (15–40 um) provide the best resolution of terminal puncta (FIGS. 6, 7, and 12). The exact extent and pattern of TSCF labeling depends on the nature of the neurotoxic insult and the ensuing survival interval. Some degeneration was seen at all time intervals examined.

The following is a more detailed description of the staining pattern observed following exposure to the following neurotoxic insults:

1) Kainic Acid—This potent excitotoxin resulted in extensive TSCF labeling within the brain. The densest labeling was found throughout the pyramidal cells of the hippocampus (FIGS. 3, 4, 15, and 16) and piriform cortex. Survival intervals of 1–4 days were optimal for revealing cellular degeneration, while terminal degeneration was optimally seen after 4–7 days. Other structures with conspicuous labeling included the dorsal thalamus (FIG. 7), the septum, the central nucleus of the amygdala, and the substantia nigra pars reticulatta. Also, portions of the cortex exhibited a patchy distribution of TSCF labeling with relatively extensive labeling of cingulate and temporal cortex regions and a more patchy distribution of layer II, III, and V pyramidal cells (FIG. 1F) throughout parietal and sensory-motor cortex (FIG. 5).

2) Domoic Acid—This seafood contaminant was relatively similar to kainic acid in terms of the resulting distribution of TSCF stained cells. Labeled cells were detected at times as short as 4 hours, or as long as 7 days after drug exposure. Lower doses of domoic acid (e.g. 1.5 mg/kg) occasionally produced a very localized patch of terminal degeneration within the stratum oriens near the CA1–CA3 boundary. This may or may not be accompanied by a few TSCF positive cell bodies.

3) Ibogaine—This antidepressant alkaloid produced a very restricted pattern of TSCF labeling. Specifically, only small clusters of labeled Purkinje cells and their dendrites could be found in the paravermal region of the cerebellum (FIGS. 2A, 2B).

4) MK-801/PCP—These NMDA receptor blocking anesthetics also resulted in a restricted TSCF labeling pattern. Specifically, small stellate cells of deep retrosplenial and cingulate cortex were positively stained.

Figure 13:
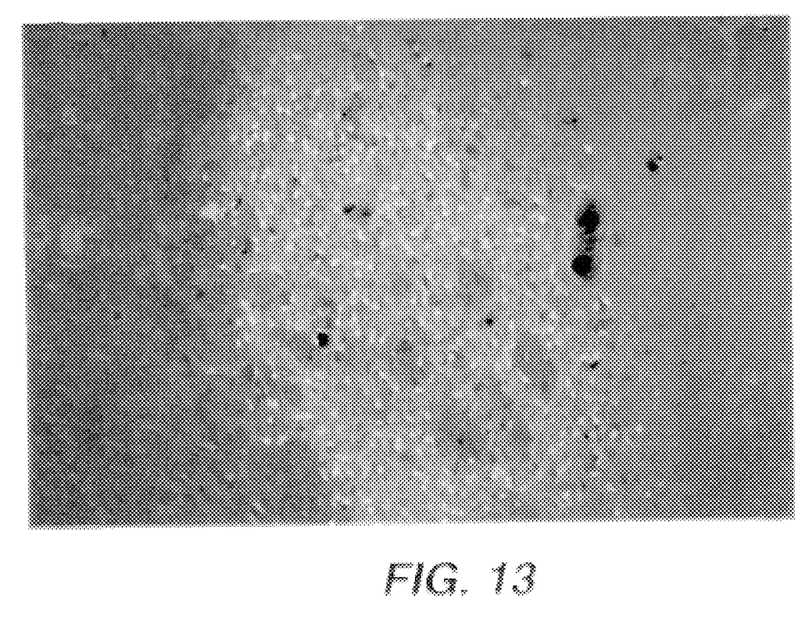
FIG. 13 is a color photomicrograph of brain tissue following treatment with 3-NPA, and after staining with an anionic fluorescein homologue of the present invention, revealing extensive degeneration of neurons and neuropil throughout the basal ganglia including the ventral half of the striatum illustrated here, while surrounding tissue and the penetrating myelinated fiber bundles are unstained; FITC filter; Mag. bar=400 um.

5) 3-NPA—Administration of this inhibitor of metabolic respiration resulted in extensive degeneration throughout the basal ganglia (FIG. 13), the thalamus, the hippocampus (mostly CA1), the deep nuclei of the cerebellum, and the cochlear nuclei. 3-NPA induced degeneration was typically characterized by a staining of virtually all neurons and neuropil within a specific structure or substructure. Degenerating cell body profiles were most apparent following a one-day survival interval, while degenerating axonal profiles were most apparent following a five-day survival interval 6) MPTP—a single dose resulted in labeled fusiform cells throughout the substantia nigra pars compacta and the ventral tegmental area in the mouse (FIG. 1H).

7) STEREOTAXIC INJECTION OF MULTIVALENT METALS—The injection of iron or manganese salts into the striatum resulted in extensive TSCF labeling of the central one half to two thirds of the entire striatum. Degenerating cellular profiles could be detected against labeled neuropil. Labeled cellular profiles were most apparent around the circumference of the injection site. Iron salts produced the largest lesion, as well as a Parkinson disease-like postoperative rigidity.

Figure 11:
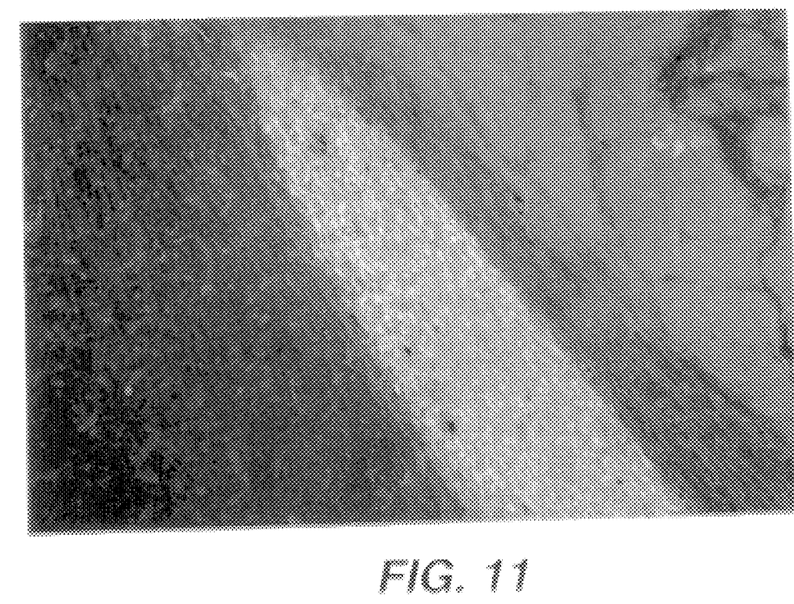
FIG. 11 is a color photomicrograph of the optic tract one week following enucleation of the contralateral eye illustrating extensive labeling of axons after staining with an anionic fluorescein homologue stain of the present invention; FITC filter; Mag. bar=200 un.

8) ENUCLEATION—Unilateral enucleation resulted in axonal label within the entire contralateral optic tract and primary terminal fields. Specifically, labeled axons within the contralateral optic tract (FIG. 11) could be followed from the optic chiasm dorsally and laterally to the lateral geniculate in which many fibers could be seen radiating amidst numerous terminal-like puncta (FIG. 12). A portion of the optic tract continued posteriorly and ended in relatively superficial terminal fields within the superior colliculus. Other nuclei in which terminal labeling could be observed were the suprachiasmatic nuclei and the medial terminal nucleus of the accessory optic system. Only the occasional labeled axon could be found in the ipsilateral optic tract. No labeled cell bodies were seen in any brain region.

9) CONTROLS—Animals receiving only saline exhibited an absence of TSCF stained neurons, glia, neuropil, or myelin. Only the choroid plexus and the meninges were TSCF positive.

Multiple Label Studies

Figure 10:
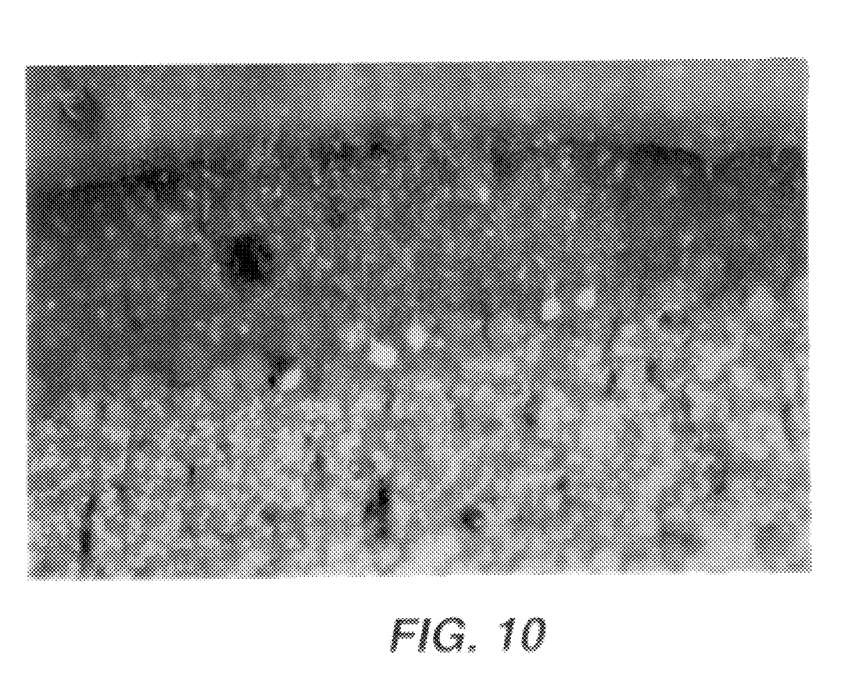
FIG. 10 is a color photomicrograph of the same region of cerebellum shown in FIG. 9 with ethidium bromide counterstain, and illustrating small orange granule cells at the bottom, larger pale normal Purkinje cell bodies, and light green and somewhat shrunken degenerating Purkinje cells; Sagittal Section; combined FITC/RITC filters; Mag Bar= 200 um.
Figure 15:
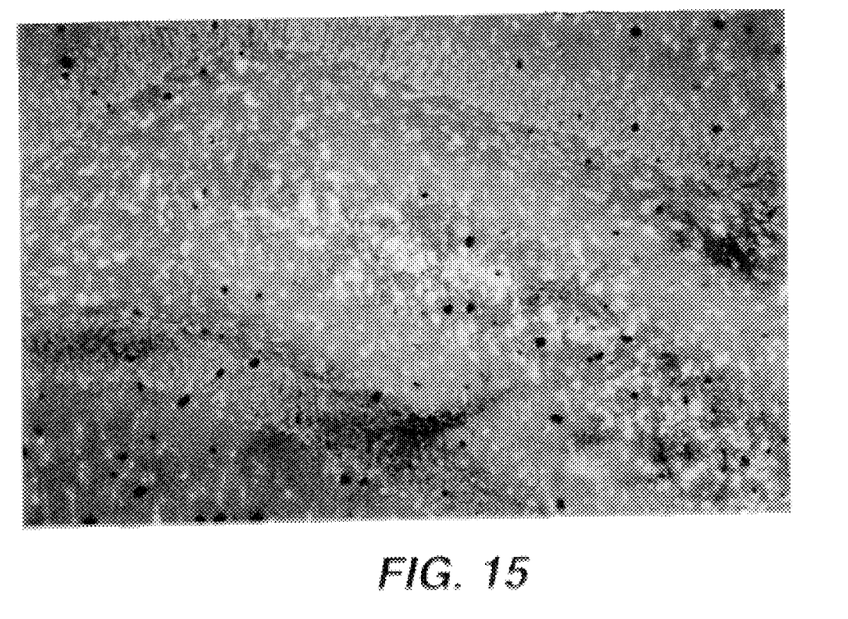
FIG. 15 is a color photomicrograph showing multiple labeling within the dentate gyrus of a kainic acid treated animal after staining with an anionic fluorescein homologue stain of the present invention and revealing both degenerating and healthy neurons, an ethidium bromide counterstain resulting in all granule cells emitting a red color. Centrally labeled polymorph cells of the hilar region emitting a light green color; combined FITC/RITC filters; Mag. bar=200 um.
Figure 16:
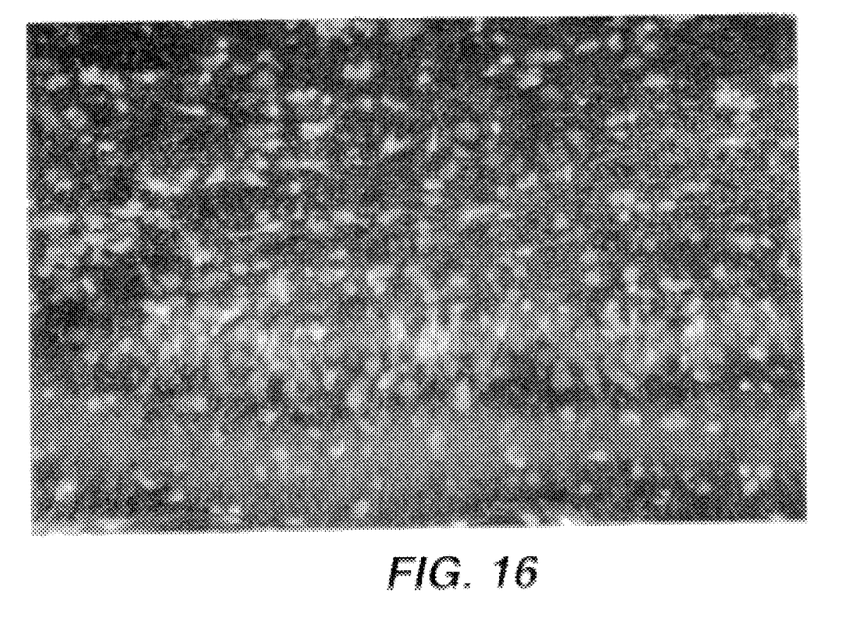
FIG. 16 is a color photomicrograph of another example of combining a fluorescent Nissl counterstain with an anionic fluorescein homologue stain of the present invention to simultaneously demonstrate healthy and degenerating neurons, in this case DAPI being used to label healthy neurons of the CA3 region, shown as a band of mostly blue cells below the middle of the figure, and some hilar cells found more dorsally, and in both regions degenerating light yellow-green positive cells being colocalized following kainic acid administration; combined FITC/wide band ultraviolet filters; Mag. bar=200 um.

1) Trisodium 5/6-Carboxyflourescein & Fluorescent Nissil Stains—This combination afforded the simultaneous localization in the same tissue section of both degenerating and viable cells. TSCF and ethidium bromide resulted in good color contrast whereby degenerating neurons appeared green, and viable neurons appeared red (FIGS. 10, 15). The TSCF background level was somewhat higher since ethidium bromide staining was not compatible with potassium permanganate pretreatment. Although DAPI was compatible with the pretreatment procedure, it served to alter the staining characteristics so that nuclear rather than Nissl staining resulted. Either counterstain contrasted well with the green TSCF labeled degenerating neurons. Unlike TSCF which stained the entire degenerating cell, the fluorescent counterstains labeled only the nucleic acids of normal cells.

2) Trisoduim 5/6-Carboxyfluorescein & Fluorescent Axonal Tracers—When "Fluoro-Gold" tracer was injected into the septal nucleus and kainic acid was subsequently administered systemically, gold colored "Fluoro-Gold" tracer retrogradely labeled hippocampal pyramidal cells were seen in the same field as TSCF labeled neurons. However, no double labeled cells were found which contained both fluorochromes. Potassium permanganate pretreatment was found to quench the "Fluoro-Gold" tracer fluorescence.

Figure 14:
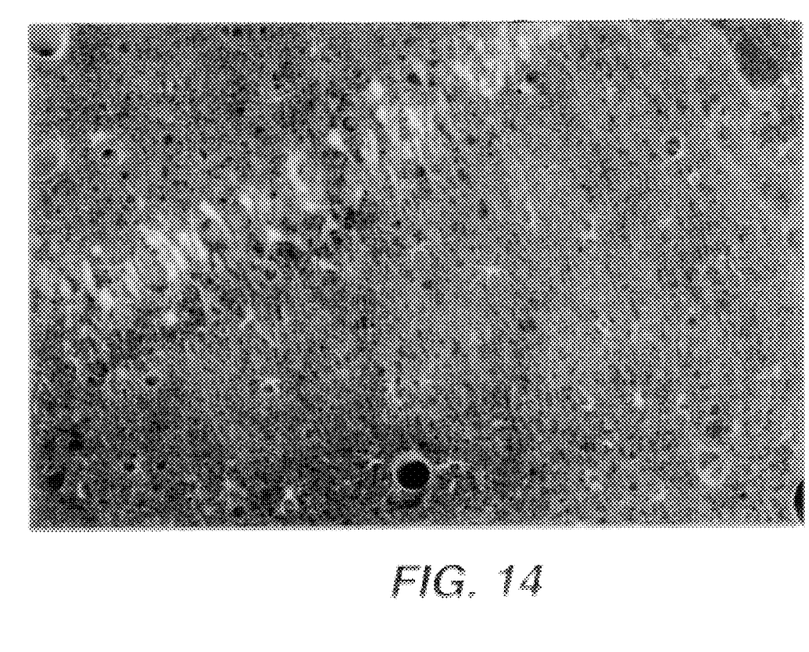
FIG. 14 is a color photomicrograph of a kainic acid treated section after staining with an anionic fluorescein homologue stain of the present invention and illustrating multiple labeling of degenerating neurons in the CA3 region of the hippocampus, while activated astrocytes appear red following immunofluorescent localization of GFAP with a rhodamine conjugated secondary antibody; combined FITC and RITC filters; Mag. bar=200 um.

3) Trisodium 5/6-Carboxyfluorescein & Immunofluorescence—Activated glial astrocytes were localized in the hippocampus with an antibody directed against GFAP. A rhodamine conjugated secondary antibody resulted in red colored astrocytes while TSCF labeled degenerating neurons appeared green (FIG. 14). GFAP staining was most intense in regions surrounding degenerating neurons, although GFAP labeled astrocytes were not observed immediately adjacent to degenerating neurons. Potassium permanganate pretreatment moderately reduced the intensity of the GFAP immunoreactivity.

The foregoing demonstrates that trisodium 5/6-carboxyfluorescein embodying the present invention can be used for the simple and reliable demonstration of degenerating neurons and their processes. This conclusion is based largely on the close correlation observed between the labeling pattern seen with TSCF and the pattern of argyrophilia seen with an ideal suppressed silver stain. This correlation holds true for all neurotoxic insults examined including kainic acid, domoic acid, 3-NPA, ibogaine, PCP, MK-801, MPTP, intracranial injection of manganese or iron salts, or enucleation. For example, when adjacent kainic acid treated tissue sections are stained respectively with suppressed silver and TSCF, the distribution and staining of cells, dendrites and terminals is virtually identical. One relatively subtle difference is that brain regions which are so necrotic that the tissue is only partially intact, such as the pyriform cortex of kainic acid treated animals or the core of the striatal lesion of a 3-NPA treated animal, can be detected with TSCF but remain unstained with the cupric-silver method. TSCF also stained degenerating myelinated fiber tracts (e.g. optic tract, fimbria) better than cupric-silver methods. Concerning nonspecific staining, silver methods can stain a number of elements artifactually including subcellular elements, myelinated tracts and neuropil. This is in contrast to TSCF which in addition to labeling degenerating neurons will only stain certain non-neuronal elements adjacent to the brain surfaces (e.g. meninges and choroid plexus).

A relatively large and diverse selection of neurotoxic insults validates TSCF's ability to detect neuronal degeneration arising from a variety of different mechanisms. Neuronal cell death was detected by the following insults and their respective putative mechanism of action: 1) kainic acid and domoic acid which are believed to act by excitotoxic mechanisms via interaction with the NMDA receptor, 2) iron and manganese compounds which are thought to act by the generation of oxidative free radicals, 3) MK-801 and PCP which act to block NMDA receptors, 4) ibogaine which is thought to produce excitotoxic damage to select Purkinje cells via activation of the inferior olive, 5) 3-NPA which blocks oxidative respiration via inhibition of succinate dehydrogenase, 6) MPTP which is converted to MPP+ and then sequestered by the dopamine uptake system where it is thought to inhibit mitochondrial complex 1 and 7) enucleation which results in Wallerian degeneration of axons and terminals throughout all primary optic nuclei. Thus, it appears that regardless of the mechanism by which a nerve cell dies, it will be labeled by TSCF.

It is also apparent that TSCF stains degenerating neurons in their entirety including cell bodies, dendrites, axons and terminals. Although terminal-like puncta were frequently observed near or adjacent to degenerating neurons, it was necessary to prove unequivocally that the puncta observed were actually axon terminals, and not merely fragments of the dendritic arborization of nearby labeled neurons. Enucleation was therefore used to demonstrate axon and terminal label in the absence of cellular or dendritic label.

The exact mechanism by which TSCF stains degenerating neurons is not known. However, some inferences can be made concerning the histochemical specificity of TSCF based on its chemical properties. For example, degenerating neurons presumably expresses a strongly basic molecule since it has an affinity for the strongly acidic TSCF, and an aversion for the basic dyes used for Nissl counterstaining purposes. Such an electrostatic interaction would be consistent with the observation that acid fuchsin can serve as a Brightfield stain of degenerating neuronal cell bodies in paraffin processed tissue, as well as the observation that a number of acidic dyes may stain degenerating neurons, although low resolution, high background levels, or rapid fading limits practical applications. It also seems likely that this "degeneration molecule" is actually produced during the degeneration process and is not simply a normally occurring molecule that labels only when the TSCF gains access via a disrupted plasma membrane. This is inferred from the observation that treatments which can permeabilize membranes (e.g. freezing, solvent extraction, and detergent exposure) fail to alter the characteristic staining patterns. Another property of this putative "degeneration molecule" is that it is resistant to solvent extraction and strong oxidation by potassium permanganate.

Potassium permanganate pretreatment not only suppresses background staining, but also significantly reduces fading of the fluorochrome. However, a drawback associated with such pretreatment procedure may occur during multiple label studies since exposure to potassium permanganate may eliminate or degrade fluorescent counterstains, immunofluorescent tags or axonally transported fluorochromes. Concerning multiple labeling studies with the retrograde axonal tracer "Fluoro-Gold," it appears that degenerating neurons do not retain the fluorochrome since populations of neurons containing either TSCF or "Fluoro-Gold" tracer are frequently seen, but double labeled cells are never observed.

TSCF does, however, appear to have a number of advantages over traditional silver methods. For example, TSCF is fast and simple. The stain requires no more than an hour, as opposed to the cupric-silver technique which typically involves two days of intensive labor. Suppressed silver methods also typically require long (weeks to months) post fixation intervals to minimize background staining. Most silver methods also are limited to a relatively small number of loose sections which are processed individually. This is in contrast to TSCF in which large numbers of slide mounted sections can be processed simultaneously. Another significant advantage of TSCF is its reliability. This is in contrast to suppressed silver methods which are notoriously capricious in nature. Another advantage associated with TSCF over silver methods is its suitability for multiple label studies. Silver methods do not generally lend themselves to multiple label studies since the extensive histochemical processing tends to preclude most other histochemical techniques and because the opaque silver reaction product tends to mask other bright field labels.

The trisodium 5/6-carboxyfluorescein and the tetrasodium 5,6-dicarboxyfluorescein of the present invention are primarily used for the detection and localization of dead and degenerating nerve cells in histological sections. This may cross over many different disciplines within the broad area of neuroscience. For example, it can be used by neurotoxicologists to determine whether an agent of interest has the potential to kill brain cells (which will not recover or regenerate) in experimental animals. It also allows them to identify the specific brain regions and individual cell types involved. Pharmacologists can use these anionic fluorescein homologues to evaluate the neurotoxic potential of a new drug, or use it to validate the efficacy of putative neuroprotective agents.

Other less common applications could include use by anatomists to infer neuroanatomical connections by lesioning a brain and then examining the degenerating efferent axons. Another more minor application is the application to human biopsy or autopsy tissue to diagnose human neurological conditions.

These anionic fluorescein homologue dyes reflect the presence of nerve cells (neurons) which were dead and degenerating at the time of the animal's death and brain removal. The dyes are exposed only to post mortem brain slices. This is completely different from the so-called "in vitro" or "live/dead assays" which can only be used on cultured living cells or on brain slices containing viable cells. These techniques depend on exposing certain dyes to viable in vitro cell preparations. Such techniques depend on differential metabolic functions (e.g. the ability of live cells to exclude a dye, or to enzymatically alter a dye) to differentiate between living and dead cells. Unlike the composition of the present invention, they do not reveal if neurons were undergoing degeneration prior to the animal's death, but rather indicate if isolated cells are actually alive at the time of dye exposure.

While certain illustrative embodiments of the present invention had been described above in considerable detail, it should be understood that there is no intention to limit the invention to the specific forms and modifications disclosed. On the contrary, the intention is to cover all modifications, alternative compositions equivalents and uses falling within the spirit and scope of the invention as expressed in the appended claims.

What is claimed is:

1. The method of detecting neuronal degeneration in postmortem brain slices, comprising staining said slices with a fluorescein compound having the formula:

wherein $R_1$ and $R_2$ are selected from the group consisting of —COOX, —H (provided that both do not=—H), and and X is selected from the group consisting of Na⁺, K⁺, Li⁺, and NH₄⁺.

2. A fluorescein compound for use in the detection and localization of degenerating neurons in post-mortem brain slices having the following structure:

wherein $R_1$ and $R_2$ are selected from the group consisting of —COOX, —H (provided that both do not=—H), and and X is selected from the group consisting of Na⁺, K⁺, Li⁺, and NH₄⁺.

3. The method of detecting neuronal degeneration in post-mortem brain slices comprising staining said slices with a fluorescein compound having the following structure:

4. A fluorescein compound for use in the detection and localization of degenerating neurons in post-mortem brain slices comprising a compound having the following structure:

5. The method of detecting neuronal degeneration in post-mortem brain slices comprising staining and slices with a fluorescent compound having the following structure:

6. A fluorescein compound for use in the detection and localization of degenerating neurons in post-mortem brain slices comprising a compound having the following structure:

7. The method of producing the compound:

comprising the steps of:
  suspending one gram of 5/6-carboxyfluorescein in 10 ml of distilled water;
  adding with stirring 3.4–3.6 ml of 9% NaOH to produce a solution having a final pH between 7.0 and 8.0 with the carboxyfluorescein fully dissolved; and
  removing the water to produce deep red crystals with metallic green iridescence.

8. The method of producing the compound:

comprising the steps of:
producing a suspension of 5/6-carboxyfluorescein in distilled water;
adding with stirring an amount of NaOH sufficient to produce a solution having a final pH between 7.0 and 8.0 with the carboxyfluorescein fully dissolved; and
removing the water to produce deep red crystals with metallic green iridescence.

9. The method of claim 8 wherein said water is removed by heating and maintaining said solution at about 40° C.

10. The method of claim 8 wherein said water is removed by vacuum lyophilization.

11. The method of claim 8 wherein said crystals are pulverized and stored in a desiccator at room temperature.

12. The method of simultaneously producing the following two compounds:

and comprising the steps of:
pulverizing and mixing together two moles of resorcinol with one mole of 1,2,4,5-benzenetetracarboxylic dianhydride; heating the mixture to 180° C. and maintaining said temperature for two hours; cooling and pulverizing the fused mass; mixing said cooled, pulverized mass with distilled water to form a 10% suspension; adding to said suspension a 9% solution of sodium hydroxide in drop-wise fashion to achieve a pH of about 7.5; maintaining said solution at room temperature for about 2 hours; filtering said solution to remove any insoluble materials; and dehydrating said solution to produce dark red crystals.

13. The method of claim 12 wherein said water is removed by heating and maintaining said solution at about 40° C.

14. The method of claim 12 wherein said water is removed by vacuum lyophilization.

15. The method of claim 12 wherein said crystals are pulverized and stored in a desiccator at room temperature.

16. The method of detecting neuronal degeneration in post-mortem brain slices, comprising staining said slices with a fluorescein compound having the formula:

wherein one R group consists of COO—X and the other R group is selected from the group consisting of COO—X, 3'hydroxy-6'ketoxanthenone, and hydrogen, and X is selected from the group consisting of $Na^+$, $K^+$, $Li^+$, and $NH_3^+$.

17. A fluorescein compound for use in the detection and localization of degenerating neurons in post-mortem brain slices comprising a fluorescein compound having the structure:

wherein one R group consists of COOX and the other R group is selected from the group consisting of COOX, 3'hydroxy-6'ketoxanthenone, and hydrogen, and X is selected from the group consisting of $Na^+$, $K^+$, $Li^+$, and $NH_3^+$.

* * * * *